US008833647B2

(12) United States Patent
Berger et al.

(10) Patent No.: US 8,833,647 B2
(45) Date of Patent: Sep. 16, 2014

(54) COMPUTED RADIOGRAPHY LICENSE METHOD AND SYSTEM

(75) Inventors: Amir Berger, Kiryat Bialik (IL); Dmitry Teif, Nesher (IL); Yuval Ben-Ze'ev, Zichrom Yaakov (IL)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 13/563,777

(22) Filed: Aug. 1, 2012

(65) Prior Publication Data
US 2013/0193206 A1 Aug. 1, 2013

Related U.S. Application Data

(60) Provisional application No. 61/521,098, filed on Aug. 8, 2011.

(51) Int. Cl.
G06K 5/00 (2006.01)
G06K 19/06 (2006.01)
A61B 19/00 (2006.01)
A61B 6/00 (2006.01)
A61B 6/14 (2006.01)
G01T 1/20 (2006.01)

(52) U.S. Cl.
CPC ............... *A61B 6/5294* (2013.01); *A61B 19/44* (2013.01); *A61B 6/14* (2013.01); *G01T 1/2012* (2013.01)
USPC ............................................. 235/380; 235/492

(58) Field of Classification Search
CPC ............... G06Q 50/22; G06Q 20/3278; A61F 2002/4632; A61B 19/5244; A61B 5/0015; A61B 5/0013; A61B 6/5294; G09F 3/00
USPC ................ 235/492, 375, 380; 715/20; 705/59
See application file for complete search history.

(56) References Cited

U.S. PATENT DOCUMENTS

| 4,739,480 A | 4/1988 | Oono et al. |
| 4,960,994 A | 10/1990 | Muller et al. |
| 5,418,355 A | 5/1995 | Weil |
| 5,428,659 A | 6/1995 | Renner et al. |
| 5,757,021 A | 5/1998 | Dewaele |
| 6,359,628 B1 | 3/2002 | Buytaert |

(Continued)

FOREIGN PATENT DOCUMENTS

| EP | 0 727 696 B1 | 5/2003 |
| GB | 2 456 452 A | 7/2009 |
| WO | 2007/118591 | 10/2007 |
| WO | 2008/060242 A1 | 5/2008 |

OTHER PUBLICATIONS

International Search Report mailed Jan. 31, 2013 for International Application No. PCT/US2012/049255, 2 pages.

*Primary Examiner* — Thien T Mai

(57) ABSTRACT

A method for licensing a system for obtaining an X-ray image of a subject. The system employs flexible information carrier plates for computed radiography, which are exposed to X-rays and then scanned in a scanner. A license media is provided with a RFID transponder, which stores in its memory identification information referring to the system components as well as information referring to an amount of valid licenses available for use of the system components. When the identification information stored in the memory of the license media RFID transponder matches the identification information transmitted to the scanner by a processing and acquisition station the carrier plates are scanned automatically.

22 Claims, 17 Drawing Sheets

(56) References Cited

U.S. PATENT DOCUMENTS

| | | |
|---|---|---|
| 6,381,416 B2 | 4/2002 | Manico et al. |
| 7,095,034 B2 | 8/2006 | Haug et al. |
| 7,211,785 B1 | 5/2007 | Berger et al. |
| 7,319,396 B2 | 1/2008 | Homanfar et al. |
| 7,518,518 B2 | 4/2009 | Homanfar et al. |
| 2004/0049733 A1* | 3/2004 | Kerr et al. .................... 715/512 |
| 2006/0133609 A1 | 6/2006 | Rodriguez et al. |
| 2006/0219964 A1 | 10/2006 | Mochizuki et al. |
| 2007/0001852 A1 | 1/2007 | Jalkanen et al. |
| 2007/0244825 A1* | 10/2007 | Semmer et al. ................ 705/59 |
| 2008/0061153 A1* | 3/2008 | Hickle et al. .................. 235/492 |
| 2009/0212107 A1 | 8/2009 | Crucs et al. |
| 2010/0104065 A1 | 4/2010 | Eguchi |
| 2012/0001737 A1 | 1/2012 | Berger et al. |

\* cited by examiner

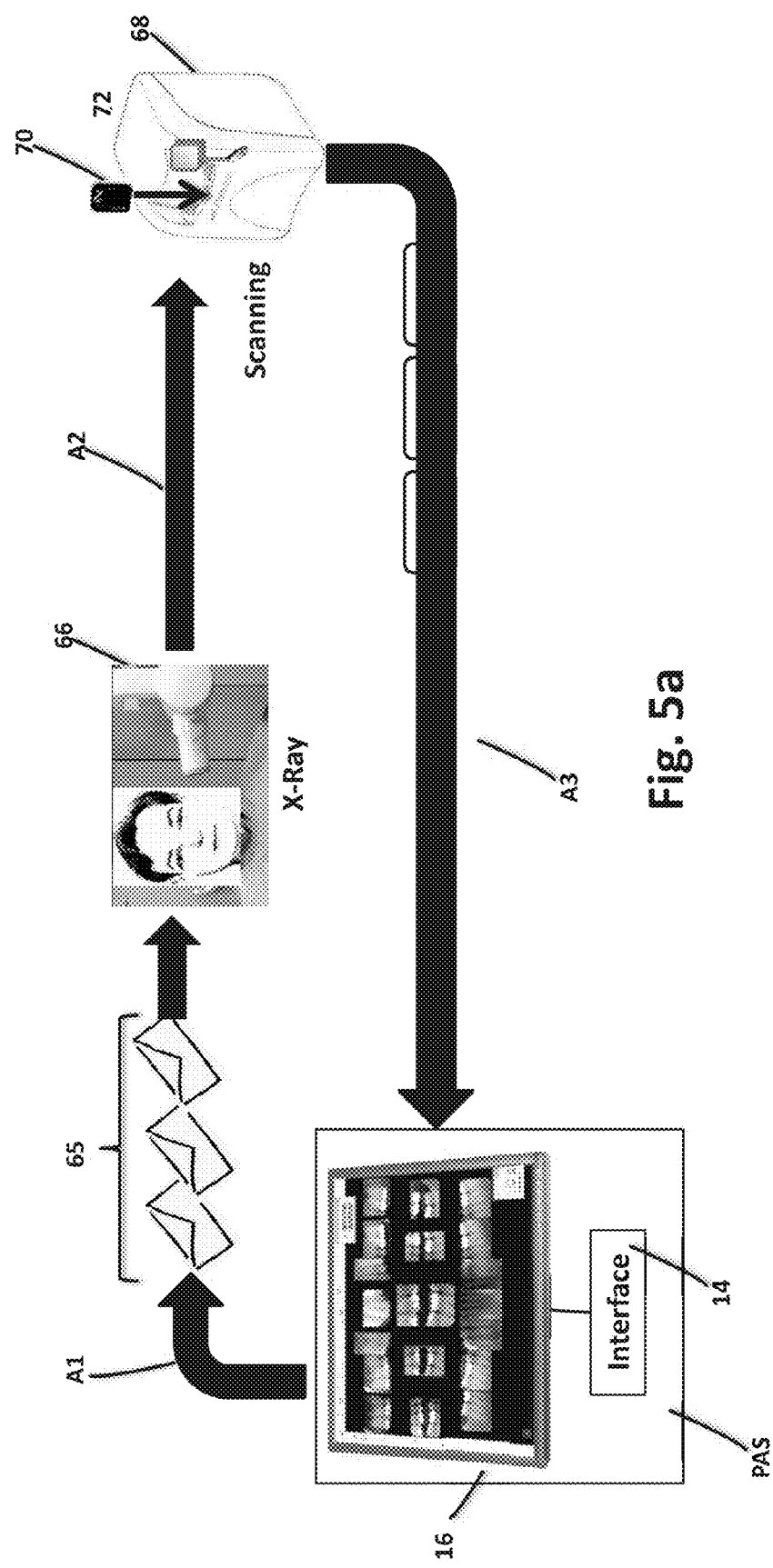

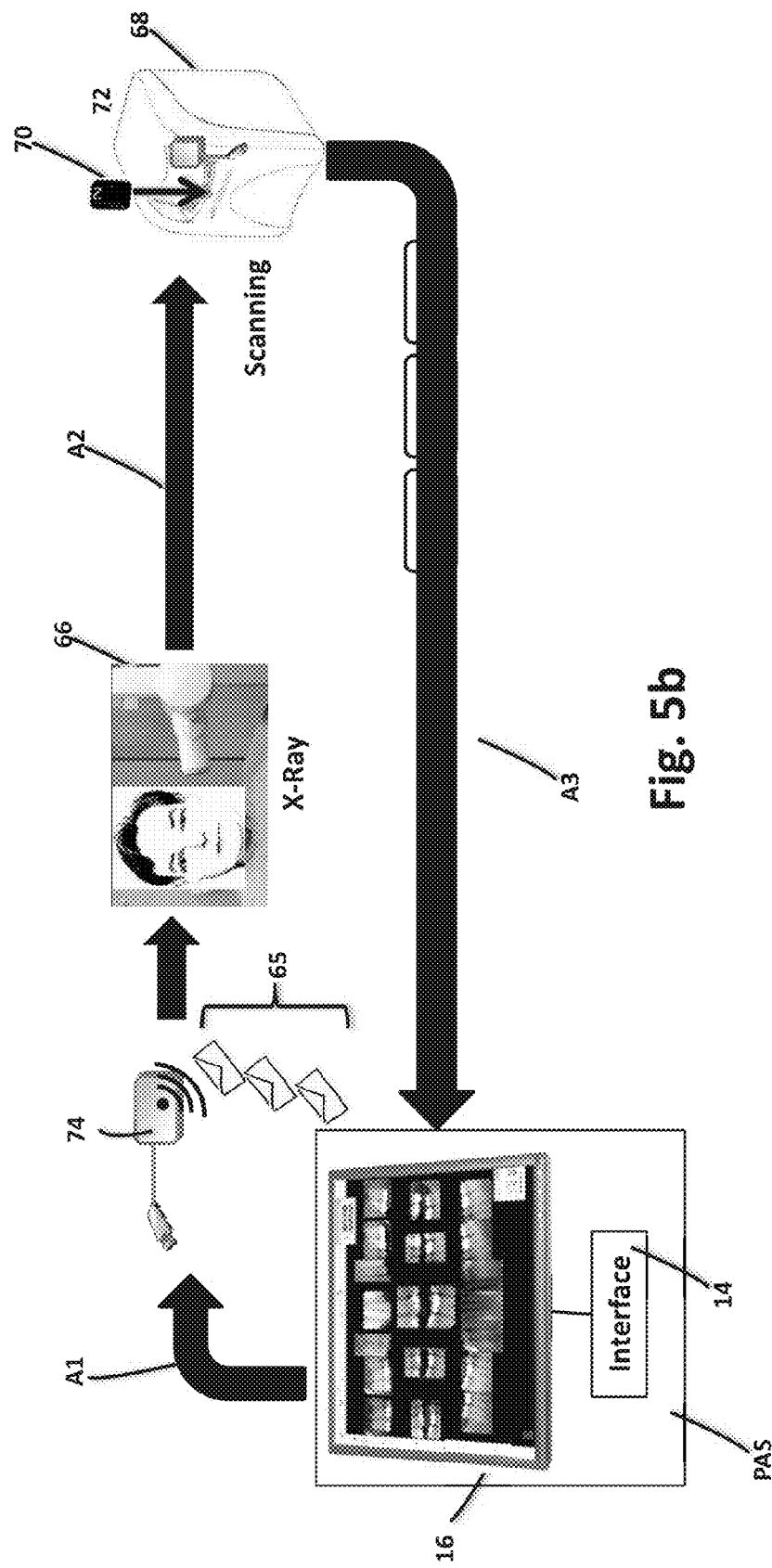

| 1. RFID ID | <Unique #> | | | | |
|---|---|---|---|---|---|
| 2. License # | [1..n] — 720 | | | | |
| 3. Tagging Device #1 | Encrypted RFID #1 ID — 730 | | | | |
| 4. Tagging Device #2 | Encrypted RFID #2 ID — 740 | | | | |
| 5. Tagging Device #3 | Encrypted RFID #3 ID — 750 | | | | |
| 6. Scanner | Scanner SN — 760 | | | | |

Fig. 7a

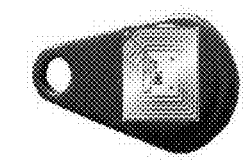
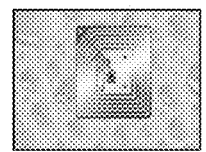
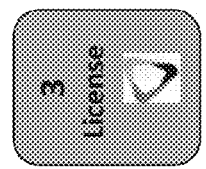
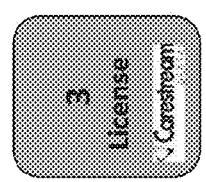
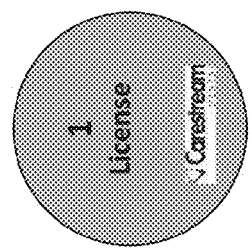
Fig. 9

COMPUTED RADIOGRAPHY LICENSE METHOD AND SYSTEM

CROSS REFERENCE TO RELATED APPLICATIONS

This application claims priority to U.S. Ser. No. 61/521,098 titled METHOD OF LICENSING THE USE OF A SYSTEM FOR COMPUTED RADIOGRAPHY, filed on Aug. 8, 2011, in the name of Berger et al, incorporated herein in its entirety.

FIELD OF THE INVENTION

The present invention relates generally to the identification of medical items to prevent their unauthorized use.

BACKGROUND

The use of information carrier plates (also referred to as phosphor plates or phosphor storage plates) for obtaining visually perceptible contrast upon exposure to X-rays is known in the art as computed radiography (CR) and is described for example in U.S. Pat. No. 7,211,785 (Berger), incorporated herein by reference.

The imaging cycle employing such plates comprises juxtaposing the plate nearby a specific part of the body (e.g., leg, arm, tooth, and the like) and then exposing the plate to X-rays in order to obtain an image from stored radiation energy. Following exposure, the plate is then removed from the patient and the latent image that is stored thereon is scanned by a laser beam or other energy source to stimulate emission of the stored energy and to form corresponding image data from the emitted energy. After the plate has been scanned, the obtained image data can be displayed and stored for further examination. The exposed and scanned plate is then erased and can be reused in a subsequent imaging cycle.

It can be appreciated that each plate is preferable to properly tracked throughout the imaging cycle as the plate circulates from X-ray exposure, to scanning, to erasure, and to re-use. That is, at each stage in this process, to know specific plate identification information as well as patient identification information and identification information concerning specific treatment with which a plate is associated.

This is preferred for general medical computed radiography (CR) and becomes especially complex for intra-oral dental computed radiography applications. In dental clinics, large numbers of patients undergo X-ray examination, and therefore a large number of information carrier plates can be in circulation at any one time, thus increasing the probability for mismatch between a particular plate and the patient and treatment data associated with the plate, as well as with the obtained image on the plate. The probability for mismatch is high in a working environment where several treatment rooms, each equipped with an X-ray generator, share the same scanning device. A mismatch can result in confusion, delay, waste, incorrect diagnosis, and the need to repeat an exposure in some cases. Other possible errors that can occur due to mismatch include inadvertent re-exposure of a plate that has not yet been erased.

The likelihood for error and the impact of an error can be further compounded when a full mouth scan is executed. This dramatically increases the number of plates used for a particular patient and requires careful tracking to avoid mistakes.

With intra-oral dental computed radiography, the mismatch between CR plates is not easily detectable by the technician, since different teeth can have a relatively similar appearance. The likelihood of confusion is high when compared with other medical radiography applications that image larger or more distinctive parts of the body about which there can be much less confusion.

Thus, positive and unequivocal identification, as well as monitoring and tracking of information carrier plates, is desired in computed radiography in general, and in intra-oral dental computed radiography in particular, since it helps to prevent patient mismatch and other errors.

There have been a number of attempts to address this issue. One example can be found in U.S. Pat. No. 5,428,659 (Renner) describing digital memory configured as a PCB (printed circuit board).

In intra-oral dental computed radiography, the exposed information carrier plates are usually placed on a flat holder that is divided into cells referring to different teeth. A technician puts the CR carrier plates on the holder such that a certain plate occupies a certain cell. The pattern of the cells corresponds to the pattern of a template that is filled in by the dental practitioner before submitting the plates to X-ray exposure. The plates are moved from the treatment station to an X-ray station and then to a scanning station, lying on the holder in the order corresponding to the template pattern. In particular situations, this arrangement can be unreliable, for example, the plates can fall from the holder during handling. Their correct re-attribution to the corresponding cell can be complicated if the plates are not provided with some type of identification means.

Radio Frequency Identification Devices (RFID devices) are known for identification, tracking, and monitoring of various items. RFID tracking is used for identifying various items, like consumer goods, reusable and disposable items, people, animals, and the like. This identification technology has been implemented in various technical and non-technical fields, including medicine.

An RFID system comprises two main components: (i) a transponder associated with an item to be identified, and (ii) an interrogator, separated from the transponder by a short distance. The RFID interrogator comprises an antenna, a transceiver and a processing device. The interrogator component sends RF energy and an interrogating signal (if necessary) to the transponder and then receives an RF response signal from the transponder. The received signal is transferred to the processing device and is read.

The RFID transponder, or so-called RFID tag, is affixed by a suitable method to the item to be identified and comprises an integrated circuit containing RF circuitry. This circuitry serves as memory for storing information to be transmitted as a signal to the processing device in the interrogator. The RFID tag also comprises an antenna for transmitting this signal. Reading the signal that has been sent by the transponder allows the item bearing the tag to be identified and monitored.

There have been attempts to implement this technology in computed radiography. Some examples are noted below.

U.S. Pat. No. 7,319,396 and U.S. Pat. No. 7,518,518, both to Homanfar, et al., describe using an RFID tag.

U.S. Pat. No. 7,095,034 (Haug) describes image carriers enclosed in cassettes, with an RFID tag affixed to the edge region of the cassette.

U.S. Pat. No. 5,418,355 (Weil) describes storage media enclosed in a cassette wherein the media is provided with an identification bar code.

U.S. Pat. No. 4,739,480 (Oono) describes a label adhered to the image storage panel, with the panel stored in a cassette. The information carried by the label represents an identification code assigned to the panel. U.S. Pat. No. 6,359,628, U.S. Pat. No. 5,757,021 (Dewaele) and EP Patent No. 0727696

(Dewaele) describe media contained in a rigid cassette with an RFID tag attached to a specific location on the cassette.

U.S. Pat. No. 4,960,994 (Muller) describes media that is used in association with a cassette and with a memory affixed to the cassette in a predetermined location. U.S. Pat. No. 6,381,416 (Manico) describes use of an RFID tag in association with photographic film used in consumer photography, for example, for establishing conditions to be selected for processing of the film.

While such arrangements may employ RFID devices to help support the use of X-ray cassettes, however, there can be little or no improvement to the workflow process for dental imaging. Persistent problems such as inconsistent labeling of plates, poor tracking of plate usage, and potential mismatch of images to patients continue to impede workflow efficiency in large dental practices.

In U.S. Ser. No. 12/976,011, entitled METHOD AND SYSTEM FOR COMPUTED RADIOGRAPHY (Amir) which published as US Publication No. 2012/0001737, there is described a method and a system with workflow process which can be employed for dental imaging. The system employs an RFID interrogator, also referred to as a tagging device. The system employs imaging plates provided with RFID transponder and a scanner provided with RFID interrogator. By means of the tagging device, the required temporary information, e.g. patient identification information, is written in the transceiver component affixed to imaging plates.

Depending on the implementation, aspects associated with marketing of such a system could arise, for example, if the system comprises more than one tagging devices intended for use in a clinic provided with a single scanner or with several scanners.

For example, a dealer can purchase four tagging devices by a discounted price of three and then to sell them to four clinics while always charging full price for each tagging device. Similar situation can arise when spare parts are sold by the manufacturer at a discounted price to the dealer.

This situation could be prevented for example by providing the system components with an identification means bearing identification information and selling the system and/or its components with a license media bearing this tag. The identification information would refer inter alia to the amount of licenses available for those components which are permitted for use.

By virtue of this provision it would be possible to link the identification information with certain tagging device and/or with certain spare part and/or with certain scanner. When this link is established the use only of those components of the system or its software would be permitted which are covered by a purchased license.

Furthermore, during the use of such a system a situation can arise, when the entire scanner or its controller board should be replaced due to malfunction. In this situation when the replace scanner is installed the calibration parameters and/or other set up parameters associated with the malfunctioning scanner would be lost and their resetting would be required for the replacing scanner. Here again it would be desirable to provide the scanner with an identification tag storing the unique setting parameters and which could be easily transferable to the replacing scanner.

There have been attempts to deal with similar issues in various technological fields. Some examples are noted below.

WO 2007118591 describes an accessory kit for use with a software based medical resource to perform a particular medical procedure. This kit includes a package, a license media with license key information and an item for performing the medical procedure. One type of license media used is an RFID tag.

US 2006/133609 describes an authentification apparatus equipped with authentification tag and a reading and recording drive that includes a transmitter and a coupler chip. The authentification tag and the transmitter are capable of communicating when the reading medium or the recording medium is coupled to the reading or recording drive.

US 2007/001852 describe wireless rights management, e.g. programs by using an RFID tag with authorization information.

GB 2456452 describes software copyright protection and licensing system using RFID. A RFID tag is supplied with a software package. During installation of the software package in a computer, a RFID reader interrogates the RFID tag for a product installation and licensing key. During installation of the software, an installation signature is generated and stored in the RFID tag and computer.

While there have been attempts to employ RFID technology for securing access to a system, there is room for improvement in providing an RFID solution for a license media tailored for specific workflow requirements of computed radiography in general and dental computed radiography in particular.

SUMMARY OF THE INVENTION

The present invention is intended to provide simple, convenient and reliable solution for identifying, monitoring and tracking flexible information carrier plates used for example in intra-oral dental computed radiography as well as for preventing unauthorized access to and use of components of a dental computed radiography system implementing this solution.

Another object of the present invention is providing a new method and system substantially for dental computed radiography employing RFID tags that can be attached to flexible information carrier plates and to license media.

A further object of the present invention is providing a new method and system preferably for dental computed radiography employing RFID tags, wherein memory can be loaded in wireless fashion with both permanent and temporary identification information.

Yet another object of the invention is providing a new method and system preferably for computed dental radiography employing RFID tags affixed to information carrier plates in which memory can be loaded with identification information concerning the information carrier plate itself, as well as with identification information concerning a dental treatment to be carried out.

Still another object of the invention is providing a new method and system preferably for computed dental radiography employing RFID tags affixed to license media in which memory can be loaded with identification information concerning components of the system.

Another object of the invention is providing a new method and system preferably for computed dental radiography in which the identification information concerning dental treatment comprises at least data associated with a patient and with specific conditions for examination.

Still another object of the invention is providing a new method and system preferably for dental computed radiography in which the identification information loaded in the RFID tag of the license plate comprises amount of available licenses, identification information concerning tagging device and scanner serial number.

Still further object of the present invention is providing a possibility for securing access to a system for computed radiography which is capable of obtaining an intra-oral X-ray image of a subject on a flexible information carrier plate for computed radiography.

For an understanding of the present invention as well of its benefits and advantages, reference will now be made to the following description of various exemplary embodiments taken in combination with the accompanying drawings.

BRIEF DESCRIPTION OF THE DRAWINGS

FIG. 5A shows a working cycle in which tagging of carrier plates is carried out at the scanning station.

FIG. 5B shows a working cycle in which tagging of carrier plates is carried out at the working station and at the scanning station.

FIG. 7A shows different fields in the memory of a RFID tag employed in license media of the system shown in FIG. 6.

FIG. 9 shows some examples of various types of license media for use with the system shown in FIG. 6.

DETAILED DESCRIPTION OF THE INVENTION

Figure 1:
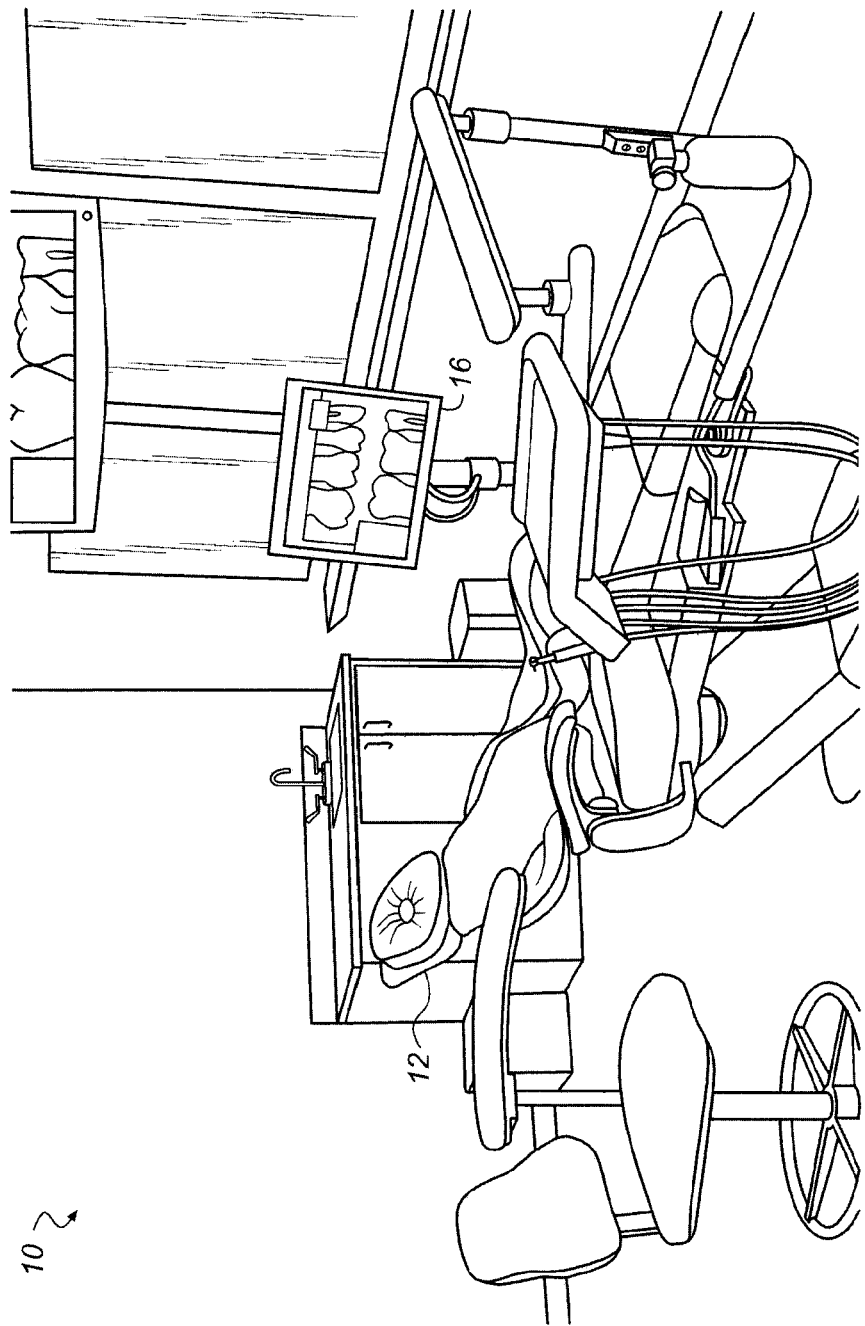
FIG. 1 shows a general treatment room used by a practitioner and provided with a chair working station.

This application claims priority to U.S. Ser. No. 61/521,098 titled METHOD OF LICENSING THE USE OF A SYSTEM FOR COMPUTED RADIOGRAPHY, filed on Aug. 8, 2011, in the name of Berger et al, incorporated herein in its entirety.

It is noted that the present invention is not limited to medical radiography in general or to intra-oral dental radiography in particular. The present invention is suitable for other medical and non-medical applications as well.

The present invention relates to identification of medical items to prevent their unauthorized use. In at least one embodiment, the present invention refers to a method of licensing the use of components of a computed radiography system employing flexible information carrier plates circulating from exposure to X-rays to scanning. In at least one embodiment, the present invention refers to a method of licensing the use of components of a dental computed radiography system while the system components are provided with identification tags and the system is provided with a license media.

In the context of the present disclosure, the equivalent terms "flexible information carrier plate", "flexible plate", "CR plate", "image plate", "imaging plate" or simply "plate" refer to photo-stimulable phosphor plates (PSP plates) that are used for image storage in the computed radiography (CR) arts, deployed in a manner analogous to the photographic plates that they have replaced in many applications. The information carrier plate is considered flexible when it has at least some degree of conformance to curvatures useful for intra-oral imaging.

In the context of the present disclosure, the term "scanner" or "scanning device" refers to a device or apparatus that is capable of obtaining stored image data from the flexible information carrier plate following exposure of the plate. The scanner typically stimulates the phosphor storage media using a laser beam. As the beam energy passes over the plate surface, it frees electrons "trapped" in "color centers" in the crystal lattice of the X-rayed phosphor plate. The light emitted during laser stimulation can be collected and the resulting signal converted into a digital image by a computer or other dedicated logic processor. The location at which the scanner is deployed is referred to as a scanning station.

In the content of the present disclosure, the term "RFID system", or "RFID device" refers to a device having two main components: (i) a RFID transponder associated with an item to be identified, and (ii) an RFID interrogator, separated from the transponder by a short distance. The interrogator comprises an antenna, a transceiver and a processing device. The interrogator component sends RF energy and an interrogating signal (if necessary) to the transponder and then receives an RF response signal from the transponder. The received signal is transferred to the processing device and is read.

In the content of the present disclosure, the term "RFID tag", or "RFID transponder" refers to a transponder that is affixed by a suitable method to an item to be identified and comprises an integrated circuit containing RF circuitry. This circuitry serves as memory for storing information to be transmitted as a signal to the processing device in the RFID interrogator. The RFID tag also comprises an antenna for transmitting this signal. Reading the signal that has been sent by the transponder allows the item bearing the tag to be identified and monitored.

In the content of the present disclosure, the term "license media" or "license plate" refers to a carrier, e.g. a substrate or a receptacle, with secured on it or within it a RFID tag.

Referring now to FIG. 1, there is shown a typical dental treatment room 10 of a practitioner. The treatment room inter alia comprises a treatment chair 12 having a console with various instruments as required for dental treatment, e.g. intra-oral treatment.

The treatment room is preferably equipped with a suitable interface terminal that serves as a processing and acquisition station for input, output, and management of data and possibly including a keyboard with mouse. It is not shown specifically but should be appreciated that the interface communicates over a network, for example, via a local Ethernet network, with a suitable server providing access to a database and a software application enabling management of medical and personal data related to a medical case. The application also allows acquisition, viewing, and processing of images obtained after scanning, archiving the images and related data, and other functions. In an alternate embodiment, such as in a small clinic, the interface may communicate with a local computer workstation or personal computer (PC), instead of with a networked server.

The treatment room is suitable for computed intra-oral dental radiography and is equipped with a monitor 16, e.g., a LCD (Liquid Crystal Display) for displaying images acquired after X-ray exposure and scanning. It is not shown in FIG. 1 but should be appreciated that a plurality of flexible information carrier plates are available, typically stored in the vicinity of the treatment chair.

It is appreciated that the treatment room can also comprise an X-ray generator, which may be situated either in the treatment room itself or adjacent thereto. In a small treatment room, a scanner can also be provided for obtaining the stored image data obtained after exposing the information carrier plates to X-rays. However location within the treatment room is not compulsory, since the practitioner can alternately use a scanner that is situated apart from the treatment room.

In the present disclosure, the treatment room is alternately referred to as a working station. If the working station is equipped with a scanner dedicated solely to this station, then the possibility for mismatch of the plates is less likely. This possibility, however, still exists and therefore it would be desirable to render the plates identifiable in some way even for such a basic system.

Figure 2:
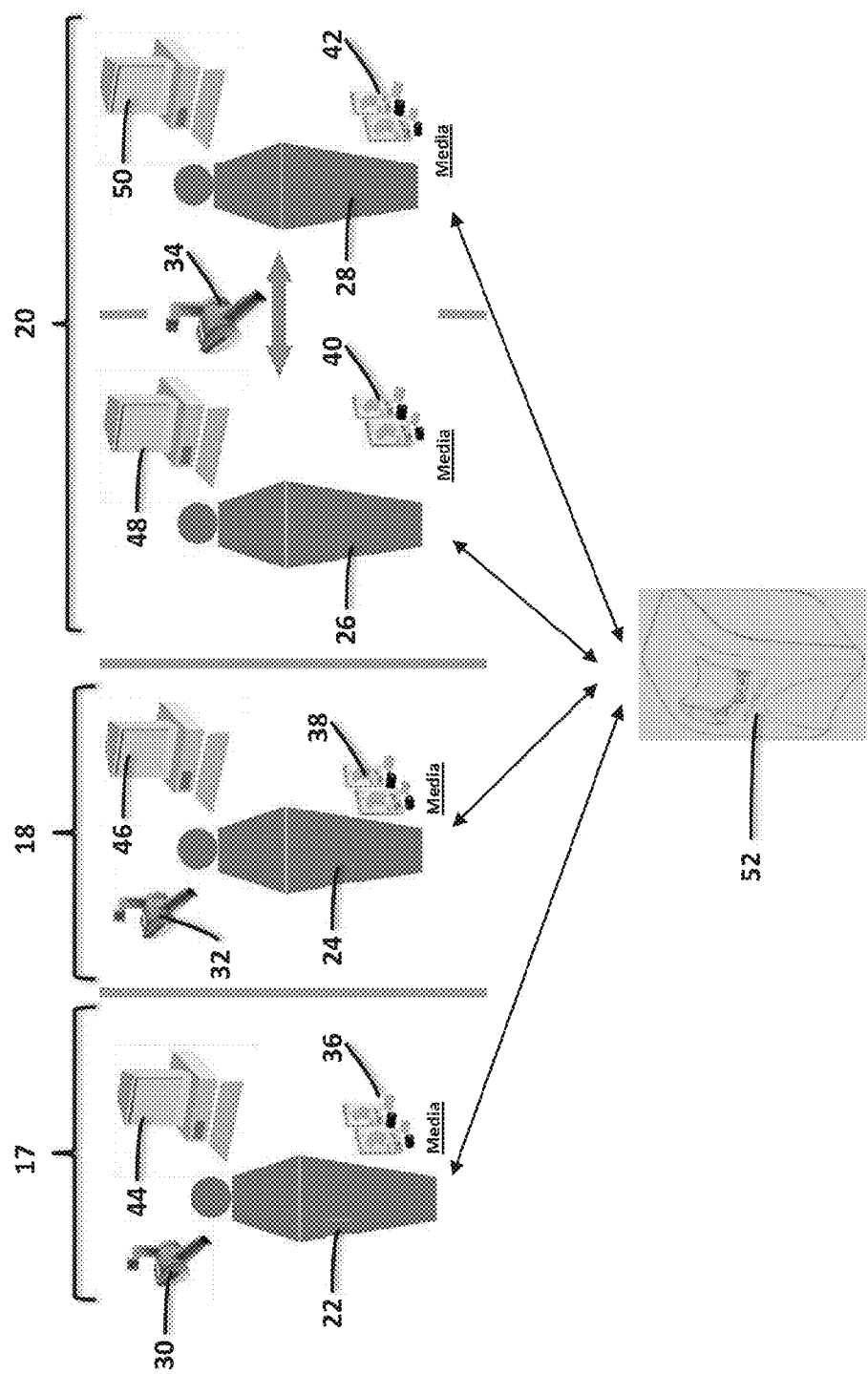
FIG. 2 depicts examples of working environment in which several practitioners occupy separate working stations and share the same scanning station.

FIG. 2 shows a schematic of another exemplary working environment for intra-oral computed radiography. This environment is more prone to mismatch than the single working station of FIG. 1 and therefore requires more careful identification of the information carrier plates. This working environment comprises a plurality, for example three, separate working stations 17, 18, 20. Working stations 17 and 18 are used by two respective practitioners 22 and 24. Working station 20 is used by two neighboring practitioners 26 and 28. Each working station is equipped with a respective X-ray generator 30, 32, 34. The generator 34 is shared by practitioners 26 and 28.

Each practitioner has sufficient stock 36, 38, 40, 42 of flexible information carrier plates, here designated as media. Each working station has a computer with respective LCD monitor 44, 46, 48, 50 and respective keyboard and mouse.

It is also seen in FIG. 2 that all working stations communicate with a common scanner 52 installed in a separate room, e.g., a disinfection room or a surgery room. This scanner is shared by all practitioners and therefore, in order to organize the workflow efficiently, the scanning step should be synchronized with the X-ray exposure step so that each practitioner reserves the scanner for plate processing before sending the exposed plates to scanning.

In an environment such as that shown in FIG. 2, a substantial number of exposed plates requiring scanning can be generated (especially where full mouth imaging is needed for one or more patients). The likelihood of mismatch is high. In the event of such a mismatch, the scanning step constitutes a bottleneck to the whole workflow. Therefore, in a working environment of this type wherein a single scanner is shared by several working stations, it is especially important to prevent mismatch between plates as they circulate between many working stations and scanner.

In accordance with the invention, the mismatch can be prevented by providing the plates with identification means rendering them immediately attributable. It would then be possible to improve the workflow and to proceed through the treatment plan more efficiently without disrupting daily operation.

In accordance with the present invention, the information carrier plates are provided with an affixed RFID transponder or tag that has a memory that can be loaded with both permanent and temporary information. The RFID tag enables memory on the information carrier plate to be in communication with a computer. Here by tagging device is meant any read/write device that is capable of reading data stored in the memory of the RFID tag as well as capable of loading the RFID tag's memory with permanent and/or temporary data and/or updating the temporary information stored in the memory. The tagging device is provided either only at the scanner or at both the scanner and the working station and is typically, but not necessarily, located near the corresponding scanner or working station, but may be separated from other equipment, such as using wireless communication. Regardless of its location, the tagging device communicates with the data management software and is automatically detected by the software. The tag's affixed memory can be loaded with the information and the stored information can be read using the tagging device.

Figure 4:
FIGS. 3 and 4 show examples of flexible carrier plates provided with RFID tags in accordance with the present invention.
Figure 3:
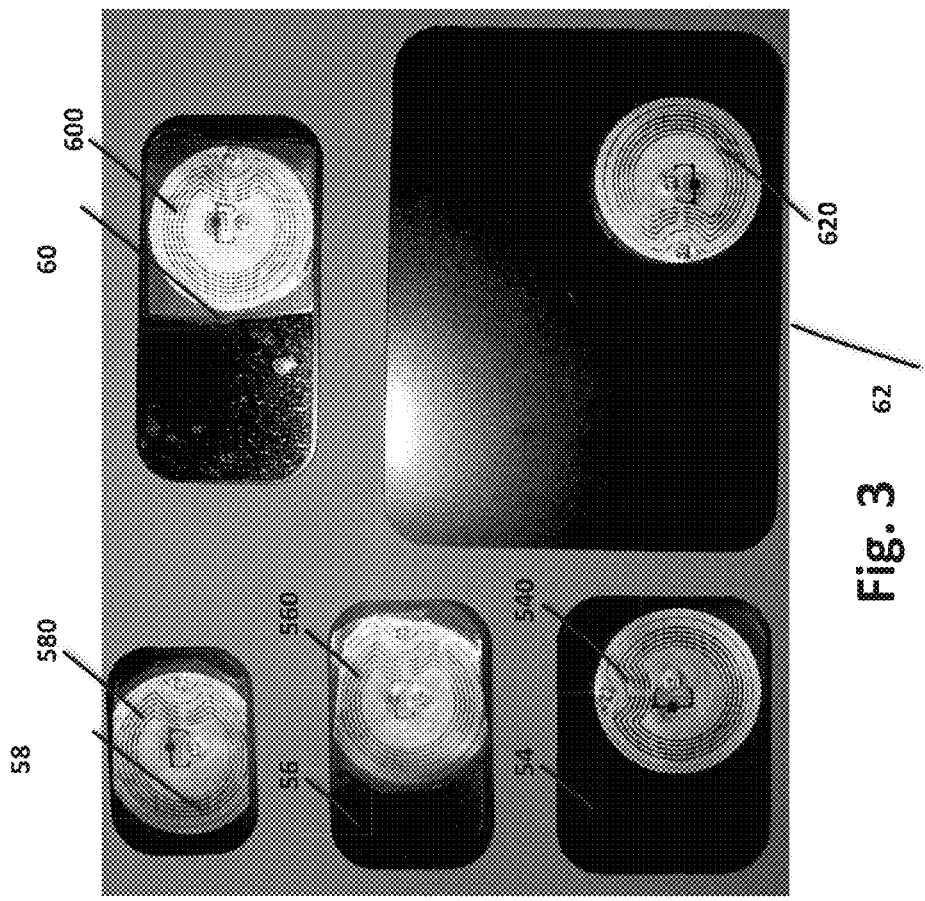

FIGS. 3 and 4 show a few examples of flexible intra-oral dental plates provided with RFID identification means in accordance with the present invention. FIG. 3 shows carrier plates 54, 56, 58, 60, 62 of different sizes. The plates are shown without disposable sachets or envelopes in which plates are normally enclosed when the practitioner places them in the patient's mouth for exposure to X-rays. Each plate bears a respective integrated circuit 540, 560, 580, 600, 620 constituting an RFID tag. The RFID tag is disposed immediately on the plate's surface and can be secured thereon by adhesive, for example. In FIG. 3, the tags are secured immediately on a rear side of the plates. The tags can be affixed to different locations of the plates depending on the plate's size. In FIG. 4, a plate 64 has an RFID tag 640 affixed immediately to a frontal side of the plate such that information about manufacturer and plate's size is also visible. FIG. 4 shows an embodiment with an RFID tag affixed to a frontal side of a plate of smaller size. It can be appreciated that, in accordance with embodiments of the present invention, the RFID tag could be affixed immediately to the rear side of a plate.

A suitable RFID tag can include a type of commercially available RFID transponder, e.g., HF 15×15 mm Dry Inlay, sales code 3001059, manufactured by UPM Raflatec, Finland. Other commercially available transponders can be used as well. A suitable interrogator can similarly be a commercially available product, e.g. HNI002 HF, manufactured by ClarIDy Solutions, Inc., Taiwan.

In FIG. 5A there is depicted an example of a working cycle suitable for information carrier plates with affixed RFID tags in accordance with an embodiment of the present invention. A processing and acquisition station (PAS) has an interface 14 coupled with monitor 16 on which are displayed images acquired during previous scanning. It is shown that a plurality of intra-oral information carrier plates 65, enclosed in disposable envelopes, proceed as shown by arrow A1, from the processing and acquisition station to X-ray generator 66. The plates intended for exposure are not yet imaged, with any previously obtained image erased from their surface after scanning. Each plate is provided with an RFID tag that has its memory loaded with permanent information referring to manufacturing data and plate size. The memory is also loaded with temporary information that can be updated by the tagging device in the course of the working cycle. Among temporary information writable in the memory of the affixed RFID tag is data such as first scan date, scan count and scan status. Scan status can include information such as Scanned and Erased or Tagged and Ready for Exposure, for example.

The plates are put in the mouth of a patient nearby the teeth to be examined. Upon completing X-ray exposure, the plates pass, as shown by an arrow A2, to the scanning station for scanning in a scanner 68. Before scanning the envelopes are removed from the plates. One such plate is designated by numeral 70; the plate itself may also include other useful information, such as a size or number indicative of size, for example. The plate is ready for insertion into the entry slot of the scanner. A tagging device 72 is deployed at the scanner, preferably housed within the scanner, and is in communication with the computer or processing and acquisition station (PAS). Tagging device 72 enables communication of the RFID tags with the computer or host workstation that is associated with the treatment room.

The tagging device has an antenna communicating with the respective antenna of the RFID tag affixed to the plate, so that information stored in the tag's memory is readable and can be available to the practitioner on the monitor of the working station or, if the scanner has a dedicated display, at the scanner itself. When the plate passes scanning the first time, the RFID read/write device writes the first scan date in the memory of the RFID tag. Upon each subsequent scanning operation, the tagging device sends a signal that is received by the antenna of the RFID tag and that increments the scan count stored in the tag's memory. This signal also updates the scan status of the plate, i.e. whether the plate has already been scanned or not. This feature makes it possible to more easily monitor the service life of the plate and its scan status. For example, the scan count can be compared against a threshold count value and the result reported when a plate exceeds the threshold. Optionally, the tagging device can be set up to disable use of a plate having a scan count above a threshold value.

When scanning is completed, the scan count is updated in the tag's memory and the obtained image is sent by the scanner to the processing and acquisition station (PAS). If the scanner is provided with a display, the image can be viewed on that display as well. Then, the plate is erased as well as the information stored in the RFID memory and the plate proceeds back to the processing and acquisition station. FIG. 5A shows schematically a plurality of erased plates proceeding back to the processing and acquisition station as indicated by an arrow A3. At the working station, the erased plates are put into disposable envelopes and are ready for the next working cycle.

The above working cycle is especially suitable for small clinics, in which the available scanner is not shared by several practitioners.

In FIG. 5B, there is shown another example of a working cycle in accordance with the present invention. This working cycle is suitable for the situation in which several practitioners share the same scanning station. In general, this working cycle is rather similar to the previous one and therefore similar elements are designated by the same reference numerals. However in contrast to the working cycle embodiment shown in FIG. 5A, the FIG. 5B embodiment provides an additional tagging device, namely secondary RFID interrogator 74. This tagging device is intended for tagging a plurality of erased image carrier plates 65 before they are put in the patient's mouth at the X-ray station. As a suitable secondary RFID interrogator one can use, for example, an Explore-R RFID reader, type HFE-00-003 manufactured by Tracient Technologies Ltd., New Zealand.

The plates are tagged while enclosed in envelopes. The tagging device, interrogator 74, communicates with the processing and acquisition station (PAS) by a suitable wired or wireless connection. It should be noted that tagging devices and interrogator devices are associated with and in communication with scanner and processing and acquisition station devices, but may be positioned at some other location rather than at these devices themselves, such as at a location that is more favorable for the workflow. In one embodiment, wireless communication between tagging and interrogator devices and their corresponding processing and acquisition station or scanner devices allows considerable flexibility for device placement.

During this working cycle, updating of information in the memory of the RFID tag takes place before scanning at the processing and acquisition station and then at the scanning station.

During the tagging step, which takes place at the processing and acquisition station (PAS), the tagging device writes temporary information into the memory of the RFID tag. The temporary information comprises inter alia, job number or other type of job identifier that relates to a particular imaging session or "job", resolution, destination address. Furthermore the temporary information comprises patient identification data that is up-loaded from the data base system, to which the processing and acquisition station has access. The patient identification data is also accessible in the data base at the processing and acquisition station. This data refers to job number or other type of job identifier, a random number written in the memory of the RFID tag. When scanning is completed and the image is sent from the scanner to the processing and acquisition station, it is displayed on monitor 16.

Now with reference to FIG. 6 an embodiment of a system for intra-oral computed radiography in accordance with the present invention will be explained. In this embodiment the system comprises the following elements:

a) a plurality of working stations 75, 76, 78 each of which is equipped with a treatment chair and X-ray generator and each having a respective processing and acquisition station 80, 82, 84 with access to appropriate application software;

b) a plurality of scanning devices 86, 88, 90 provided with respective primary interrogators 860, 880, 900;

c) a plurality of flexible information carrier plates 92 having respective RFID tags affixed immediate to one of their sides;

d) a plurality of tagging devices 800, 820, 840 associated with and in communication with respective working stations PAS 80, 82, 84 and operable for tagging information carrier plates before the plates are exposed to X-rays; and e) a server 94 providing access to a plate database 940 and appropriate data management system.

Figure 6:
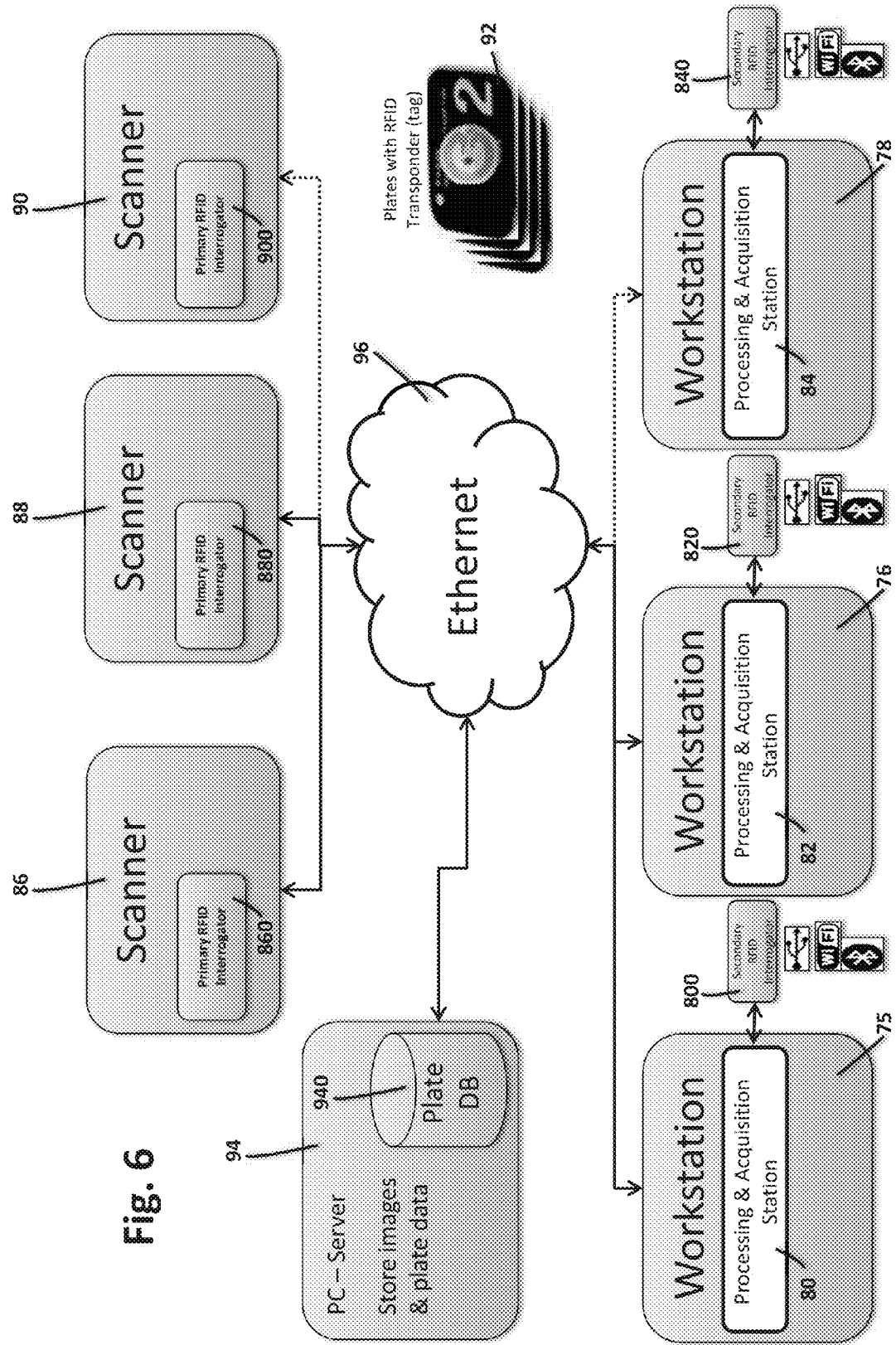
FIG. 6 depicts schematically a system for intra-oral computed radiography in accordance with the present invention.

As shown in FIG. 6, working stations, scanners, and server can communicate between each other via connection over an appropriate network, e.g., Ethernet network 96. With network connection, messages can readily be sent from the scanner to the processing and acquisition station and vice versa, as well as files with scanned images for storing the database.

In the system of FIG. 6, tagging devices 800, 820, 840 that refer to working stations 75, 76, and 78 can communicate with respective processing and acquisition stations 80, 82, 84. In one embodiment, this communication uses a USB connection. Wireless communication is available in an alternate embodiment, through WiFi (Institute of Electrical and Electronics Engineers (IEEE) 802.11 standard, generally termed WiFi) or Bluetooth connection. One should appreciate that these devices can communicate as well through any other suitable wire or wireless connection that enables exchange of data.

It is noted that the system of the present invention may have more or fewer than three working stations and three scanners as depicted in FIG. 6. For example, one can contemplate a system comprising a single working station and one scanner, or one working station and several scanners, or several working stations and one scanner. The number of working stations need not be equal to the number of scanners and vice versa. One should also bear in mind that in a configuration when the system consists of single working station and single scanner, the tagging device at the working station can be absent and such a system can function in accordance with the working cycle explained in connection with FIG. 5A. This is irrespective of the sequence in which the plates have been tagged. It is appreciated that this is advantageous since it saves practitioner time required for matching between an individual plate and the template window associated with the plate. The template and its windows are explained in more detail subsequently.

In such a system, the server and networked communication via the Ethernet are not necessary; instead, the working station itself can be equipped with a PC loaded with database, data management system, and processing and acquisition software.

It is noted that tagging devices that are provided at working stations and at scanners, and which are in communication with computer and other equipment at working stations and with scanners, are operable to both read and write or amend information stored in the memory of RFID tags in order to update it as part of the tagging operation.

It is noted that during marketing of such a system which environment may include a plurality of tagging devices and/or scanners it would be desirable to prevent unauthorized use of any of its components in order to avoid a situation when a component, e.g. tagging device, spare part or scanner which has been sold to a dealer for a discounted price is resold by the dealer to a client, e.g. a practitioner for a full price. By restricting access to the system components it would be possible to prevent possibility to buy the tagging devices "off the shelf" and use them freely. Furthermore it would be possible to have different price structure for spare parts and for tagging devices.

In accordance with the invention to prevent unauthorized use of the system components the system is provided with a license media, which comprises a RFID transponder (tag) which memory stores permanent and temporary information. The permanent information comprises amount of available licenses issued by a manufacturer to a particular system, i.e. amount of tagging devices which are permitted for use with the system. This situation might refer for example to a clinic, where simultaneously operate several practitioners sharing the same scanner, however each of them having his/her own tagging device and thus the clinic comprises several tagging devices and a single scanner. One can contemplate, of course, a situation in which several practitioners use several tagging devices and several scanners.

The temporary information stored in the memory of the RFID tag of the license media refers to identification information associated with each tagging device and with each scanner employed in the clinic. This information can be for example encrypted RFID tag number or serial number of the scanner. In practice the entire information stored in the RFID tag of the license media is encrypted.

Figure 7B:
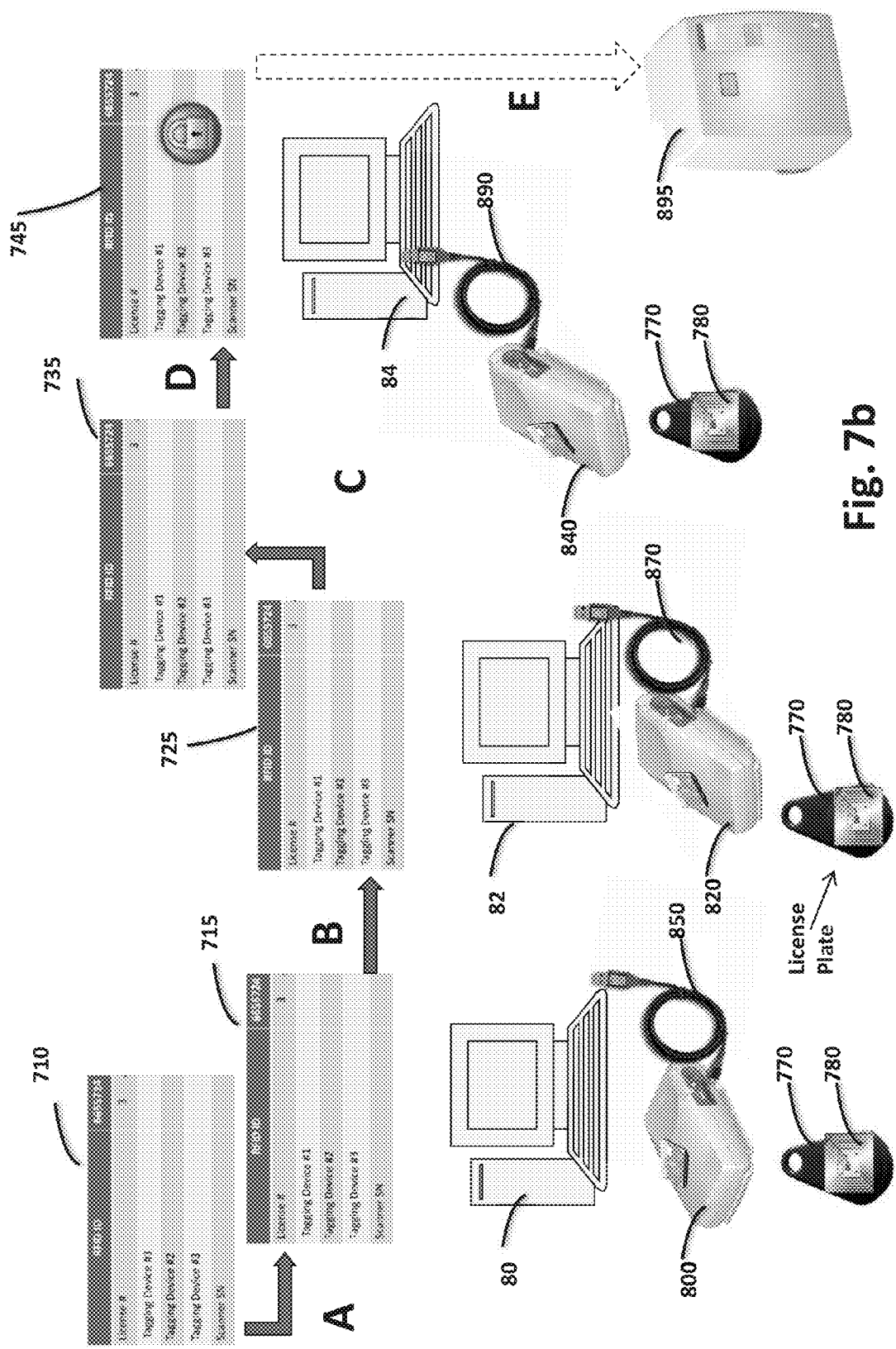
FIG. 7B depicts schematically working environment of a system provided with tagging devices and license media.

Referring now to FIGS. 7A and 7B it is shown an exemplary structure 710 of a memory of a license media. Examples of the license media will be shown further.

It can be seen that the memory structure has slots (rows) divided into columns, which together define the permanent and temporary content of the license media memory. The left column refers to a particular field (type) of the identification information stored in the memory of the RFID tag of the license media, while the right column is reserved for storing a unique value of each field. Thus memory slots 720, 730, 740, 750, 760 store designations of the fields and unique value associated with each field. So for example slot 720 is intended for storing the amount of licenses, which in this example is three, i.e. three tagging devices are permitted for use in a system. The amount of licenses can be less or more than three depending on particular deal closed by the manufacturer with a particular clinic. The number of licenses is burned by the manufacturer into license plate memory and this field is "write once" only. After burning the amount of licenses is "locked", i.e. it can be changed only by the manufacturer of the system. This information remains permanent so long as the amount of tagging devices is kept the same in the same clinic and it is unlikely that more licenses is anticipated for this clinic. If more licenses are required, a new license media will be issued.

The further slots 730, 740, 750 and 760 are allocated for storing temporary information which is associated with a first, a second and a third tagging device respectively. Slot 760 is intended for storing identification information referring to a scanner. The fields associated with these slots are "write once" and empty by default. The information stored in slots 730, 740, 750 and 760 is temporary, because each time, when tagging device or scanner malfunctions it is replaced by a new one the information referring to the replacement item should be entered in the memory of the license media.

Now with reference to FIGS. 7A and 7B it will be explained how the permanent and temporary information concerning tagging devices and scanner is entered into memory of the RFID tag of a license plate. In FIG. 7B is depicted a system, which employs three processing and acquisition stations (PAS) 80, 82, 84, each of them being in a data communication with respective tagging device 800, 820, 840 for example by a USB cable 850, 870, 890. It should be appreciated that wireless communication is available in an alternate embodiment, through WiFi (Institute of Electrical and Electronics Engineers (IEEE) 802.11 standard, generally termed WiFi) or Bluetooth connection. One should appreciate that these devices can communicate as well through any other suitable wire or wireless connection that enables exchange of data.

The system comprises also a single scanner 895, which is in data communication with each processing and acquisition station. The system further comprises a license media, which in this embodiment can be configured for example as a license card 770 bearing a RFID tag 780 thereon and the tag having appropriate flash memory. The initial condition of the transponder memory is designated by a numeral 710. It is seen that the memory comprises already burned amount of licenses, which is three and that more four empty slots are reserved in the memory structure for filling with identification information regarding three tagging devices 800, 820, 840 and scanner 895. Now the license plate is placed near the tagging device 800 and once it is switched on the data concerning identification of this tagging device is transferred to the RFID interrogator of the tagging device 800 and then it is transmitted by the interrogator to the RFID tag of the license plate for writing and storing the transmitted data into first empty slot of the license plate memory. This step is schematically designated by an arrow A. Upon completing this step the memory has a condition designated by reference numeral 715. In this condition tagging device 800 is defined in the memory of the license plate RFID transponder 780 by its unique number 22754.

In the further disclosure the above-described process of tagging the license plate will be referred-to also as "activation" of tagging devices and accordingly those tagging devices, which identification information has been already stored in the memory of the license plate transponder will be referred-to as "activated" tagging devices.

Then license plate 770 is placed near tagging device 820 and upon switching it on the identification information referring to this tagging device is transferred by the processing and acquisition station 82 into next empty slot of the memory of the license plate RFID transponder. Condition of the memory of the license plate RFID transponder is designated by the numeral 725 and in this condition the second tagging device is defined in the memory by its unique number 77722. This step is designated by an arrow B and upon its completion the second tagging device becomes activated.

Then license plate 770 is placed near tagging device 830 and upon switching it on the identification information referring to this tagging device is transferred by the processing and acquisition station 84 into next empty slot of the memory of the license plate RFID transponder. Condition of the memory of the license plate RFID transponder is designated by the numeral 735 and in this condition the second tagging device is defined in the memory by its unique number 65443. This step is designated by an arrow C and upon its completion the third tagging device becomes activated.

Once all the tagging devices are "activated" the memory slots containing their identification information are full and no more information can be written and stored into them. By virtue of this provision there is established a link between the license plate and the tagging device. It would be also beneficial if the identification information concerning the activated tagging devices is also stored in the memory of the processing and acquisition station (PAS).

The next step is designated by an arrow D and it is associated with recording and storing of the identification information referring to scanner. At this step the software of the last processing and acquisition station 84 asks which scanner should be used in association with the "activated" tagging devices, i.e. merely with those which are eligible for use according to the amount of valid licenses stored in the memory of the license card. The available scanner is selected from the software menu and its serial number or any other identification information is automatically transferred by the RFID interrogator of the tagging device to the memory of the license plate RFID transponder. The condition of the transponder memory is designated by a numeral 745. This information is also sent to the processing and acquisition station. Once this information is stored there is established unequivocal link between the scanner and the license plate. One should appreciate that this step, i.e. linking the scanner with the license plate could be accomplished before completing the storing of the identification information referring to tagging devices.

Still further step is designated by an arrow E and it is intended for establishing unequivocal link between eligible tagging devices and eligible scanner, i.e. between those components which are permitted for use according to the information stored in the memory of the license plate RFID tag.

For establishing such a link the identification information referring to activated tagging devices should be transferred to the scanner. In practice the last step can be accomplished either through connection to the Ethernet network or by inserting the license plate into scanner entry slot.

In practice the working cycle of a system having license media is as follows. First acquisition software is launched at processing and acquisition station. The software reads information referring to available tagging devices. If encrypted identification information of a tagging device is missing and therefore could not be read by the software this tagging device is ignored by the software. The consequence of this is that information stored in the RFID tag of the image plate is ignored by the scanner's RFID interrogator and user should input the information concerning target room and treatment case information manually.

If however the encrypted identification information concerning a certain tagging device is present this tagging device is acknowledged. In this situation a job file presented in the XML format is sent by the software of the processing and acquisition station to a scanner. The job file contains treatment case information e.g. patient details, treatment details, and the like, as well as identification information of a tagging device which was used for tagging the image plate and identification information of a scanner assigned for scanning.

The tagged image plates are exposed to X-rays and then proceed to scanning. Each time when a new image plate enters the scanner its RFID interrogator component compares identification information stored in the license plate with the identification information sent with the job file. If the identification information stored in the license plate matches the identification information associated with the job file the image plate would be scanned by the scanner automatically. If there is no match, the plate still can be scanned, however the scanner should be operated manually and without benefits of the rout shown in FIG. 6, i.e. without automatic attributing the study information to a scanned image obtained from a certain image plate. In other words, the system still can be used for scanning image plates, however less efficiently. In this situation the system operates in accordance with the working cycle depicted in FIG. 5A.

Figure 8A:
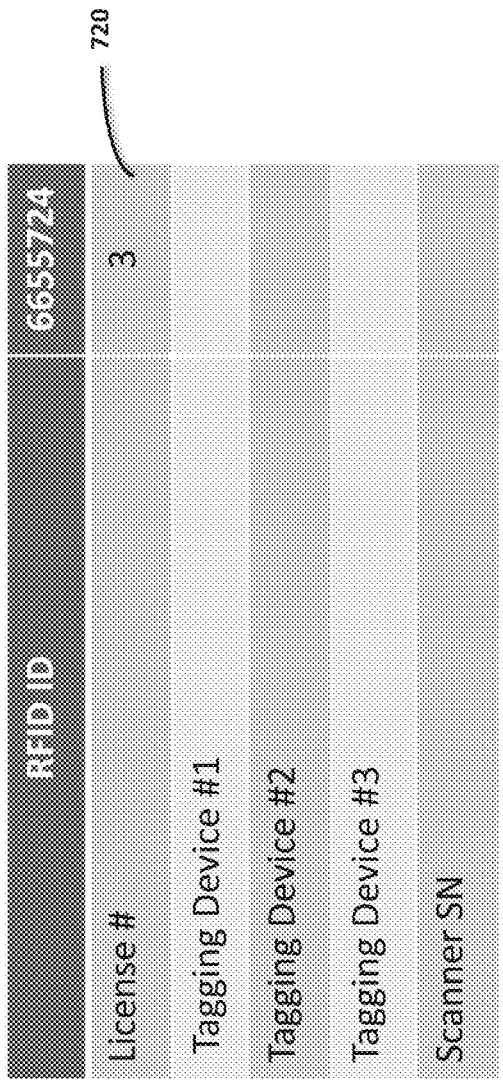
FIGS. 8A and 8B depicts schematically memory fields of the RFID tag of the license media for various amounts of licenses.
Figure 8B:
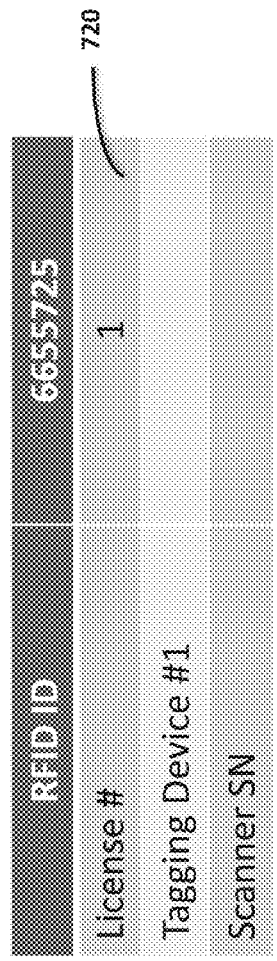

Referring now to FIGS. 8A and 8B it is seen a memory structure of the license media RFID tag in a situation when either three licenses are granted or only a single license is granted. In this situation in the slot 720 referring to the license amount field is respectively stored either number 3 or 1. It is seen that the amount of empty slots allocated for identification information of tagging devices and of the scanner is four for three licenses (three for tagging devices and one for scanner) and two for one license (one for tagging device and one for scanner).

As seen in FIG. 9 the license media can have various configuration, e.g. it can be round or rectangular. The rectangular license media can have radiused corners or sharp corners.

The license media can be configured as a flat substrate shaped as a card with the RFID tag secured thereon for example by gluing. The substrate can be made of a suitable relatively rigid plastic material and have dimensions similar to a credit card so as to be conveniently portable. In other embodiments the license media can be configured as a receptacle or a box containing the RFID tag inside it. An example of such a license media can be the iButton, manufactured by Maxim or the WibuKey manufactured by WIBU-Systems.

The RFID transponder, which can be used with the license media comprises for example Explore-R RFID reader, type HFE-00-003 manufactured by Tracient Technologies Ltd., New Zealand.

The license media can be provided with various indicia, for example with a digit indicating the amount of licenses available to the user, and/or with the name of the license provider. In FIG. 9 for example are seen license cards with indication of 1 or 3 licenses and with indication of the license provider name Carestream.

Figure 10:
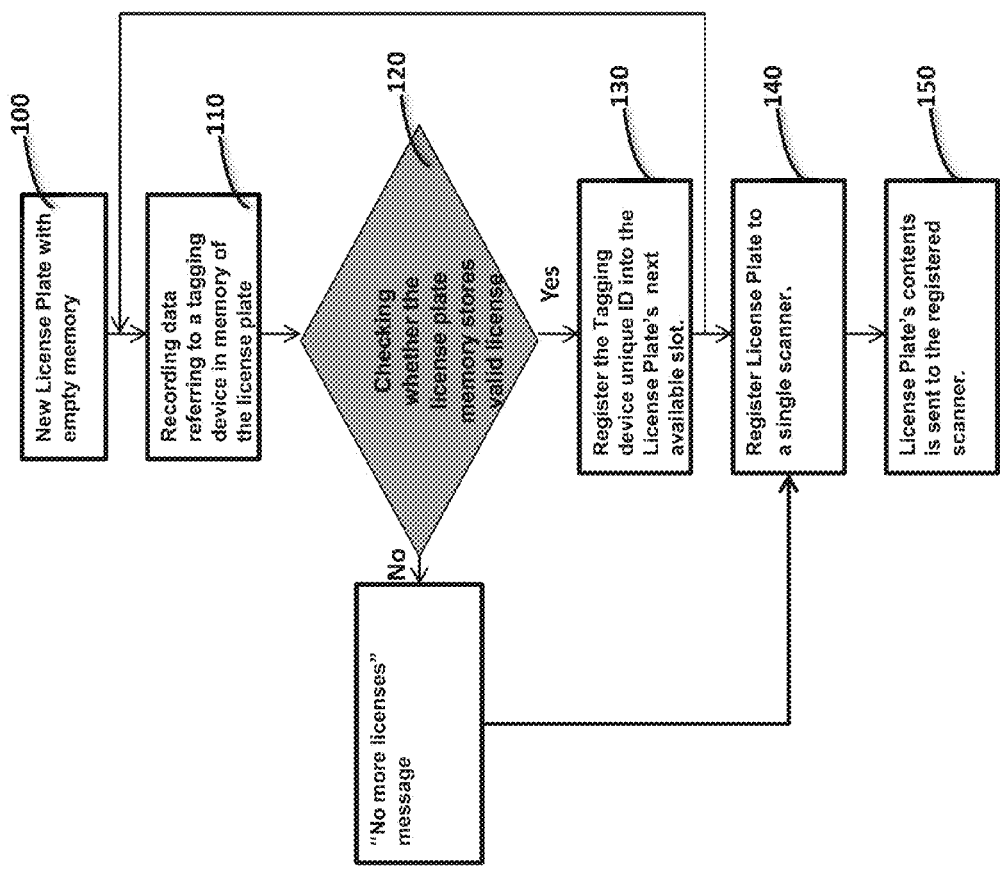
FIG. 10 shows an example of a flow chart for activation of the tagging devices in accordance with the present invention.

Referring to FIG. 10 there is shown a flow chart summarizing the process of establishing a link between permitted for use tagging devices and scanner. This flow chart illustrates an algorithm, which is executed by the processing and acquisition software in accordance with information sent to and received from the tagging devices, scanner and license plate.

There is provided a fresh license plate having RFID tag storing in its memory solely the amount of valid licenses, while the other slots of the memory are empty. This step is designated by numeral 100.

Then tagging of the license plate takes place, during which identification information concerning particular tagging device used for tagging is transferred into memory of the license plate RFID tag. This step is designated by numeral 110.

At a further step, which is designated by numeral 120, the software checks whether the license plate still has a license available for this tagging device. If the answer is NO the system proceeds to a step 140, at which scanner identification information is recorded in the memory of the license plate RFID tag.

If the answer is YES, the system proceeds to a step 130, at which unique identification information associated with this tagging device is recorded in the memory of the license plate RFID tag. Then the system returns to the step 110, at which tagging of the license plate takes place again, however this time in the memory of the RFID tag is recorded identification information concerning the next tagging device. When tagging step of all available tagging devices is completed the system proceeds to step 140.

After completing recording identification information concerning tagging devices and scanner the system proceeds to step 150 at which the identification information stored in the memory of license media RFID tag is transferred to the memory of the scanner.

Figure 11:
FIG. 11 shows an example of the memory content of the license media after completing the activation process.

In FIG. 11 is shown an example of memory content after completing recording information concerning three tagging devices and one scanner.

Figure 12:
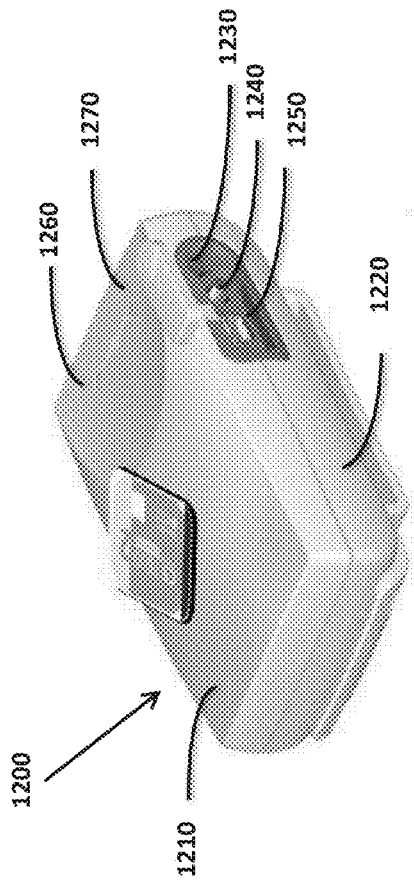
FIG. 12 is an exemplary external view of the tagging device for use in the system provided with license media.
Figure 13:
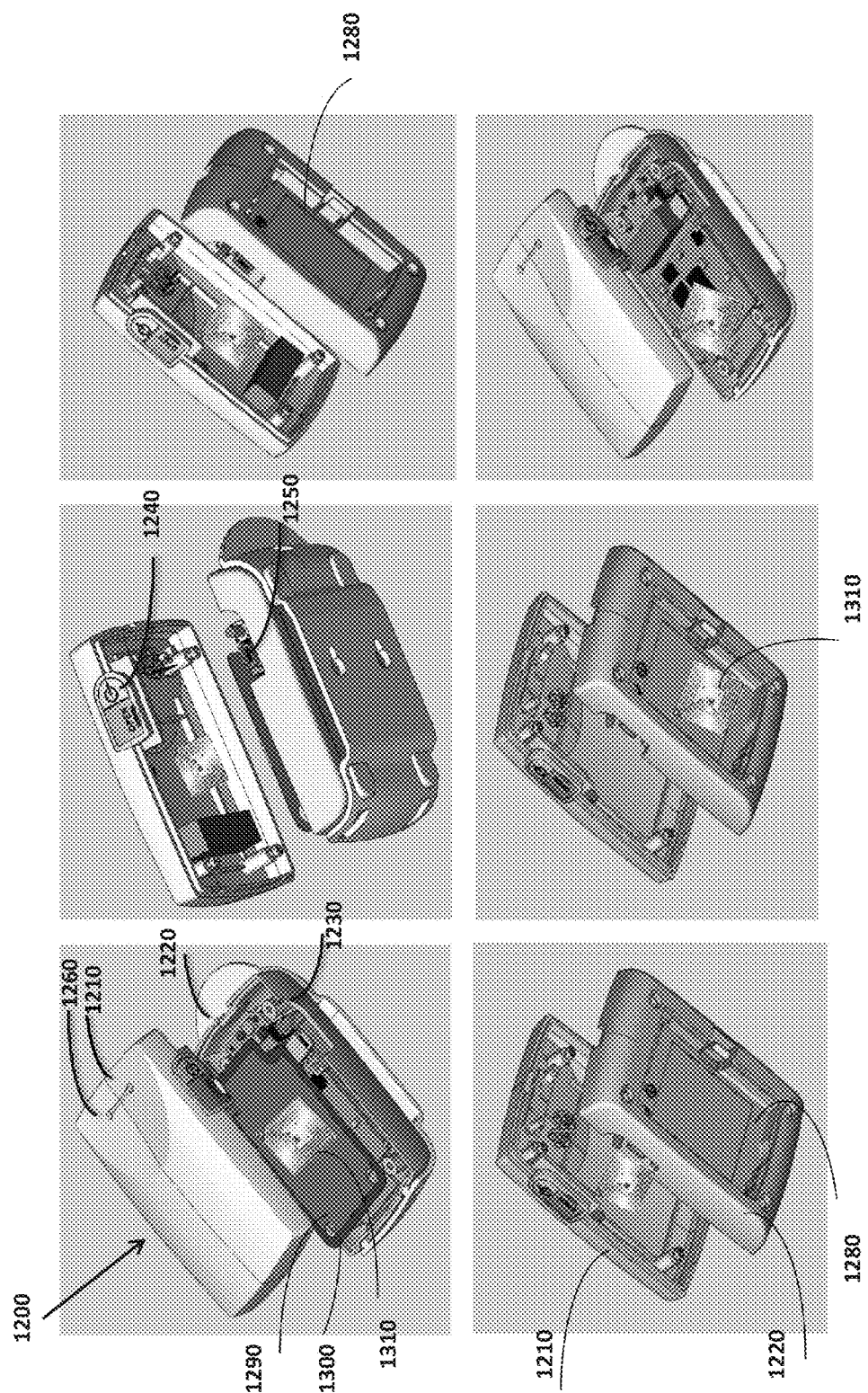
FIG. 13 shows some exploded views of the tagging device shown in FIG. 12.

An example of a tagging device for use in the system of the present invention is shown in FIG. 12 and FIG. 13. In accordance with the invention the same tagging device could be used as interrogator both for tagging the license media during the activation process and for tagging image plates before their exposure to X-rays and subsequent scanning.

As shown in FIGS. 12 and 13 the tagging device is configured as a substantially rectangular box 1200 having a cover portion 1210 and a lower portion 1220. Within the box are mounted the necessary components of the tagging device as well as a battery, which energize it. A depression 1230 is provided on one side of the box. The depression provides access to a main switch 1240 and to an opening 1250 for a USB connection.

On the cover portion there are provided two openings 1260, 1270, through which one can see light of two signal LED's, having different colors. One of the LED's signals whether the tagging device is in operating mode and the other one signals when the battery of the tagging device should be recharged. The battery (not shown) is accommodated within a niche 1280 (see for example FIG. 13) made in the lower portion 1220.

As shown in FIG. 13 the tagging device comprises mounted within the box 1200 a board 1290 with an antenna 1300 of the RFID transceiver. The board carries a RF circuitry 1310 of the RFID transceiver.

By virtue of the RFID transceiver the tagging device functions as interrogator enabling data communication with license media and image plate.

As mentioned, the license plate is tagged before using the system and its components. Upon completing the tagging step the permitted tagging devices become "activated" and are linked to specific scanner and thus the system is ready for operation.

It is recognized that sometimes the system components could malfunction and should be either repaired or be completely replaced. In this situation it would be still required to avoid unauthorized access to the replacement items.

Figure 14:
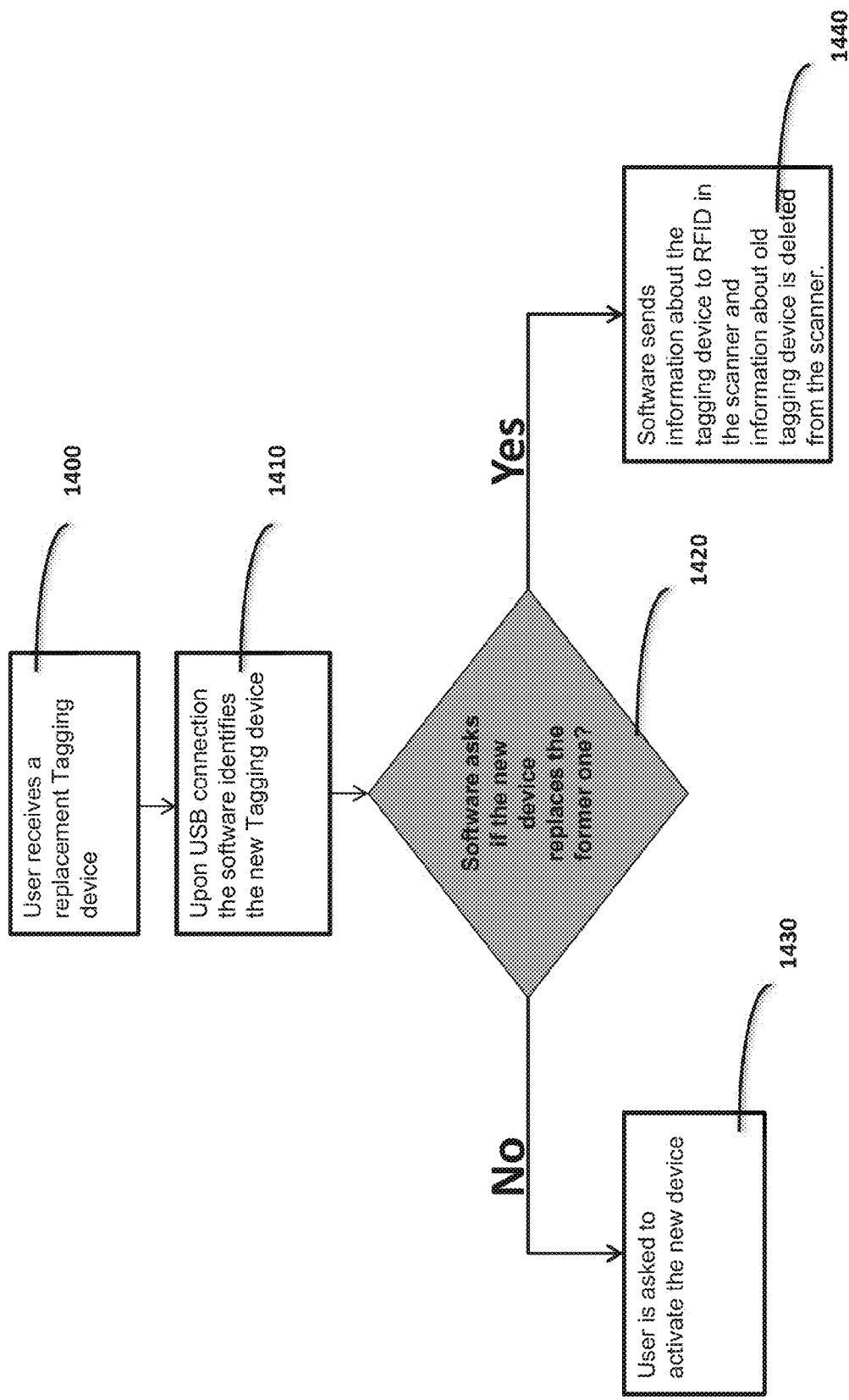
FIG. 14 shows an example of a flow chart for replacing malfunctioning tagging device.

With reference to FIG. 14 it will be explained a workflow taking place in a situation when a tagging device malfunctions and therefore should be changed by a replacement item, which can be either the same tagging device after repair or a new tagging device.

At a step 1400 a replacement tagging device is received by the user and at a step 1410 the processing and acquisition software identifies the replacement tagging device.

At a step 1420 the software inquires whether the replacement item is the new item or the repaired item. If the answer is NO, i.e. it is old tagging device but repaired, the software proceeds to a step 1430, during which the user is requested to activate the old tagging device. Without activation the repaired tagging device can't be used. If the answer is YES, i.e. it is new tagging device, the software proceeds to a step 1440, during which identification information referring to the new tagging device is sent to scanner and stored in the memory of its RFID device while previous identification information is deleted from the memory of the RFID device.

A workflow will now be explained which refers to a situation when a scanner or its controller board malfunctions. Malfunctioning can comprise many problems, like mechanical problems, e.g. impossibility to move image plate, software problems, e.g. program does not respond, scanning problems, and the like.

Herein described are two scenarios which could be taken into account. The first one is associated with a scanner, which can be switched on, however malfunctioning during its operation. The second scenario is associated with a scanner, which can't be energized at all. In either scenario the user can receive a replacement scanner.

Figure 15:
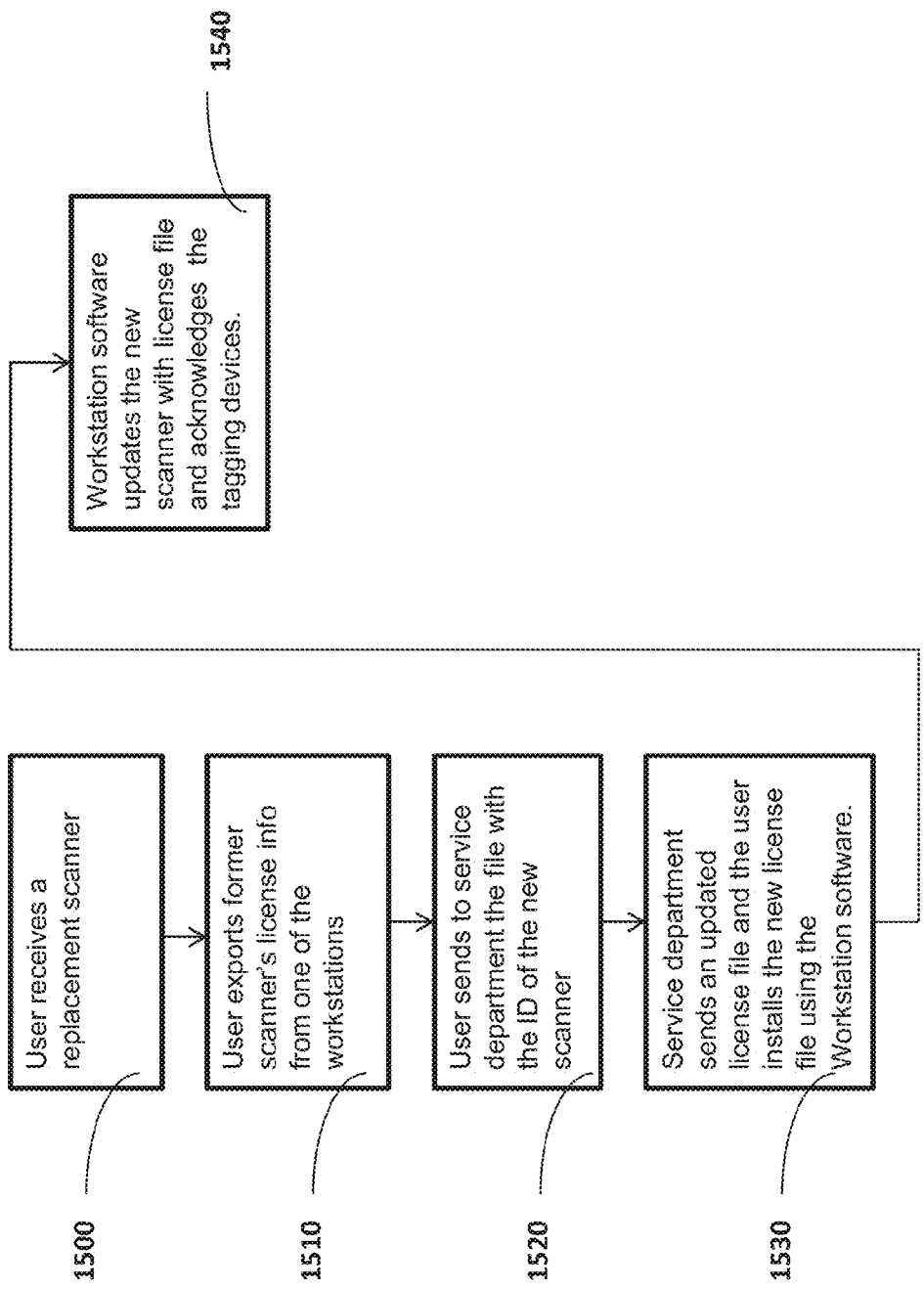
FIG. 15 shows an example of a flow chart for replacing malfunctioning scanner.

With reference to FIG. 15 it will be explained now an exemplary workflow referring to the situation when a scanner malfunctions and should be replaced. At a first step, designated by numeral 1500 the user receives a replacement scanner. At the next step, which is designated by numeral 1510 the user transfers to the manufacturer the identification information concerning the malfunctioning scanner. This can be accomplished for example by using one of the working stations, which, e.g. through the Ethernet is in data communication with the manufacturer's network.

At a further step, which is designated by numeral 1520 the user by similar manner transfer to the manufacturer identification information concerning the replacement scanner.

At a further step, which is designated by numeral 1530 the manufacturer send to the user updated license file, from which is deleted identification information referring to the old scanner. The updated license file comprises identification information referring to the replacement scanner.

At a step 1540 the processing and acquisition software updates RFID flash memory of the replacement scanner by the updated license file and by identification information referring to activated tagging devices.

By virtue of the above workflow there is possible to prevent the possibility for unauthorized use of the system components, in other words, merely an eligible replacement scanner will automatically scan imaging plates tagged by particular tagging devices.

Figure 16:
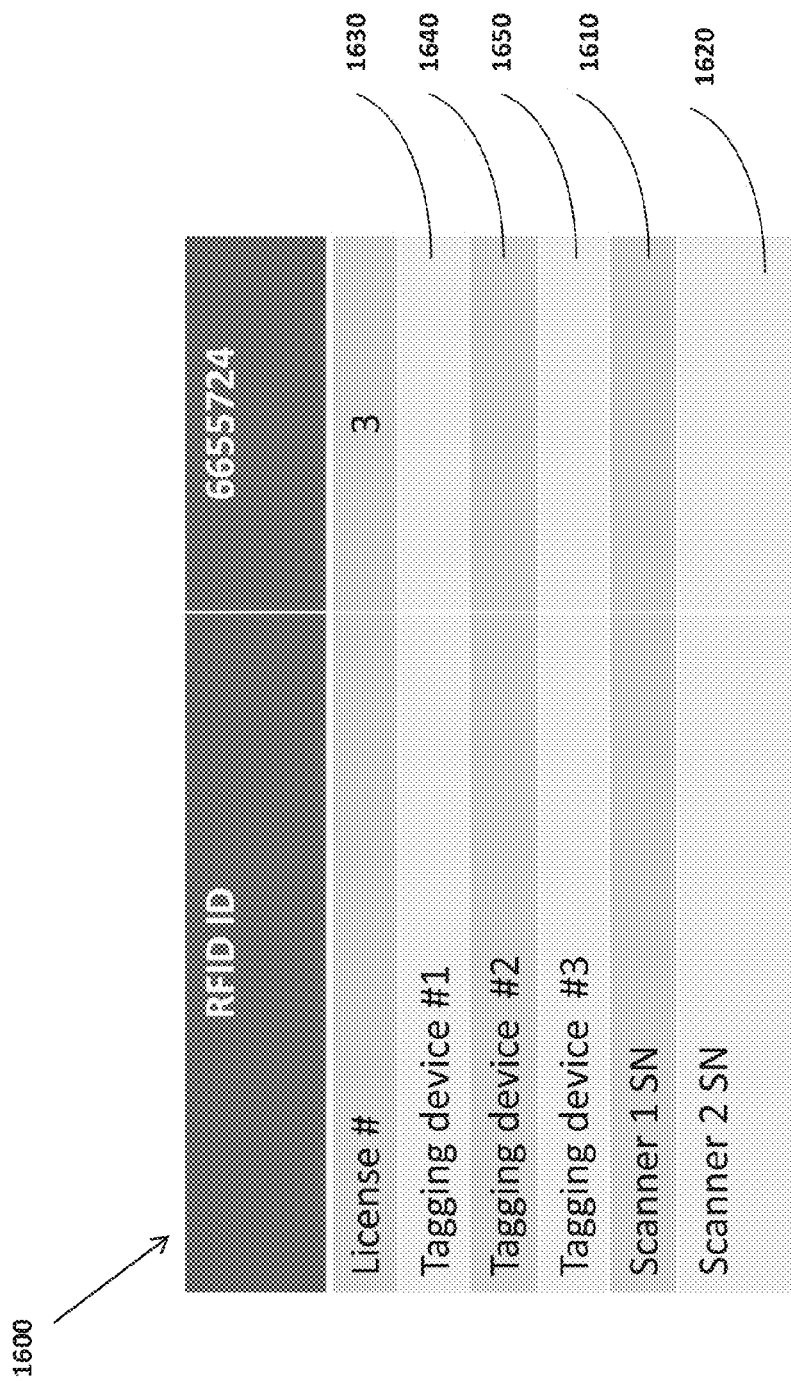
FIG. 16 shows an example of the content of memory of the license media suitable for a system provided with two scanners.

With reference to FIG. 16 it is shown a further embodiment of the invention, in which the license plate memory is provided with at least one supplemental slot. A memory structure 1600 is seen, which comprises slots 1610, 1620 allocated respectively for a scanner 1 and a scanner 2. It is also seen that the amount of licenses is three and therefore it is possible to activate three tagging devices by storing their identification information in slots 1630, 1640, 1650 allocated for three tagging devices.

It should be appreciated that in this embodiment the processing and acquisition software should be appropriately programmed to allow transferring to the license plate RFID tag memory identification information referring to more than a single scanner. An advantage of this embodiment would be a possibility for linking between particular tagging devices and particular scanner or linking all tagging devices with both scanners.

In still further embodiment each tagging device could be provided with an individual identification means, which is for example a RFID tag, storing in its memory the same identification information as in the license plate disclosed before. The individual RFID tag is a transponder, which in fact functions as an auxiliary license plate for linking between particular tagging device bearing this tag and particular scanner. In practice this auxiliary license plate is configured and dimensioned as a small, removably adherable label, which can be adhered to a location in the housing of the tagging device. An example of this location could be the niche intended for accommodating the battery. The auxiliary license plate is adhered to a tagging device with possibility for removal and transfer to other tagging device. It could be appreciated, that the processing and acquisition software recognizes the tagging device according to unique identification information of the auxiliary license plate, which is a number of the individual RFID tag. Thus in a situation when the label is removed from the malfunctioning tagging device and transferred on the replacement device there would not be required any more to activate the replacement tagging item. It can be automatically acknowledged by the processing and acquisition software as soon as it reads the identification information transmitted by the transponder.

Similarly to the above-mentioned RFID tag which can be used for attributing the tagging devices the scanner also can be provided with an individual, removably adherable RFID tag. This RFID tag would be adhered to the scanner chassis and function as individual transponder associated with the scanner. The RFID tag would store in its memory the same identification information as in the license plate as well as information concerning the scanner itself and its setup. This information comprises for example, manufacturer information, amount of scans performed, working time, configuration information, calibration information, preferences, and any other information, which should be saved during replacement of the electronic board. One can appreciate that it is advantageous to have such individual transponder secured on a scanner since during its replacement neither there is a need in activation of the replacement scanner nor its recalibration. The stored and saved on the RFID tag identification information remains intact even in a situation when the main controller board with all the electronics and software is being replaced. Upon powering the replacement scanner the stored calibration parameters will be verified and automatically detected.

Figure 17:
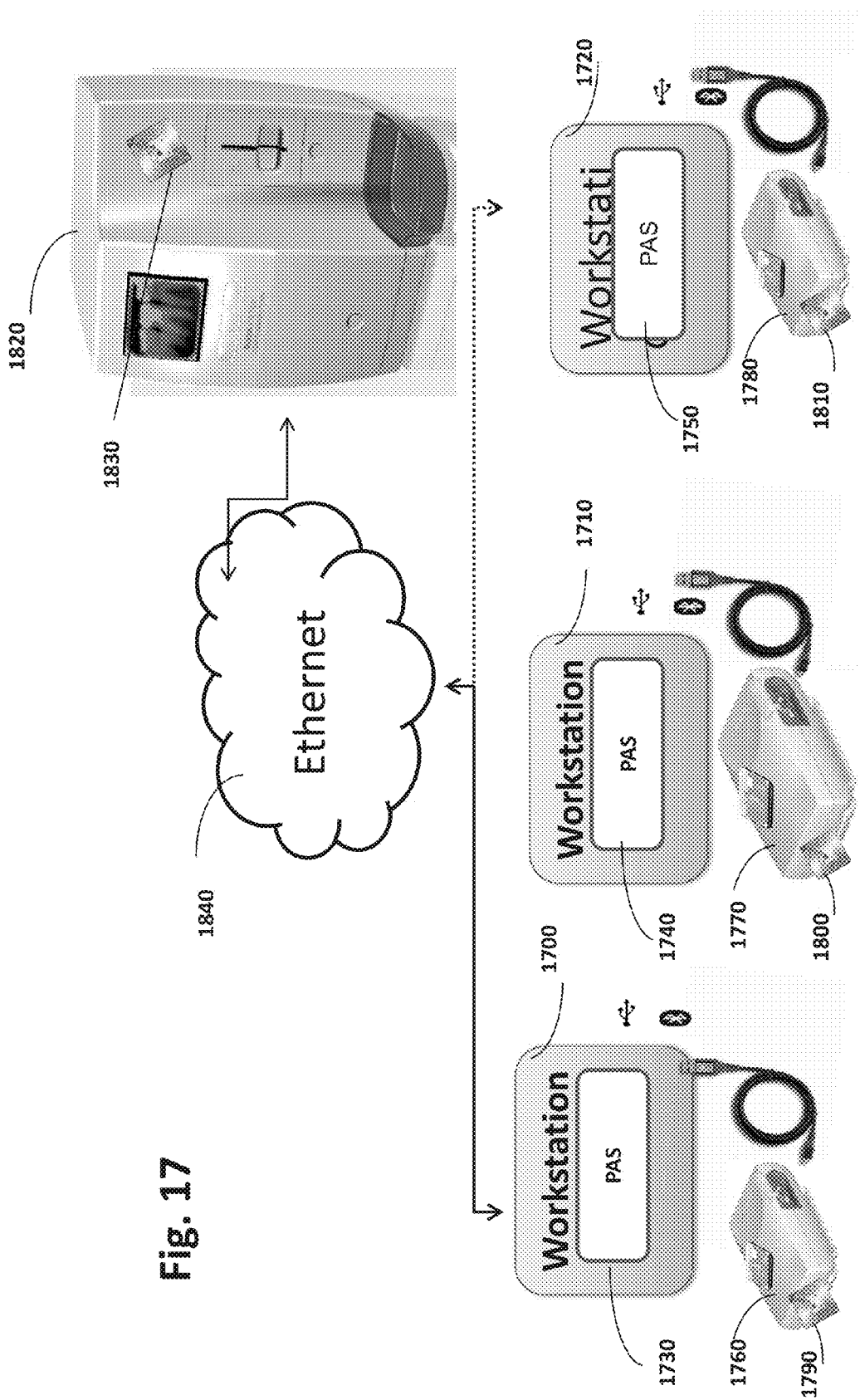
FIG. 17 shows an example of a flow chart for activation of tagging devices provided with internal license media.

With reference to FIG. 17 it is shown an example of a working environment of a system in which individual RFID tag is provided in each tagging device as well in the scanner.

The system comprises for example three working stations 1700, 1710, 1720, each of them having respective processing and acquisition station 1730, 1740, 1750, connected either via wired connection (e.g. USB), or wireless connection (e.g. bluetooth) with a respective tagging device 1760, 1770, 1780. Each tagging device is provided with a respective RFID tag 1790, 1800, 1810, which for the sake of simplicity is depicted outside the tagging device. One should appreciate that in practice the RFID tag is located within a housing of the tagging device. The system comprises also a scanner 1820 provided with an individual RFID tag 1830. For the sake of simplicity the tag is shown outside the scanner. In practice it is secured within the scanner, preferably affixed to its chassis without possibility to remove it from the chassis.

The RFID tags store in their memories preferably encrypted identification information comprising the amount of licenses available, unique identification of each tagging device and serial number of the scanner. This information has been stored during the earlier activation step and before the system begins to operate. The scanner's RFID tag stores also setup information. The components of the system, i.e. processing and acquisition stations (PAS), tagging devices and scanner communicate between them via a network, e.g. Ethernet 1840.

The invention has been described in detail with particular reference to certain preferred embodiments thereof, but it will be understood that variations and modifications can be effected within the scope of the invention.

For example, one could contemplate employing the present invention not merely in dental radiography but also in other computer radiography applications, where RFID devices are available. Such applications may include for example, but are not limited to, orthopedic radiography, chest radiography, scull radiography, spine radiography, and the like.

What is claimed is:

1. A method for the use of a computed radiography system including at least one scanner for scanning flexible information carrier plates exposed to X-rays to obtain an X-ray image of a subject, the at least one scanner having a scanner RFID interrogator with a memory, the carrier plates having a RFID transponder with a memory storing a treatment case information, the treatment case information being transferable to the memory of the RFID transponder by at least one RFID interrogator, the method comprising:

providing a license media having a license media RFID transponder with a memory for storing information;

storing in the memory of the license media RFID transponder a first information which is associated with an amount of valid licenses permitting use of the at least one RFID interrogator and of the at least one scanner;

storing in the memory of the license media RFID transponder a second information, which is associated with identification information of the at least one RFID interrogator;

storing in the memory of the license media RFID transponder a third information, which is associated with the at least one scanner;

transferring the first, second and third information to the memory of the scanner;

transmitting to the memory of the scanner a treatment case information comprising identification information associated with the at least one RFID interrogator and the at least one scanner;

comparing information transferred to the memory of the scanner from the license media with the treatment case information transmitted to the memory of the scanner; and scanning the exposed to X-rays carrier plates if the identification information transferred from the license media matches the identification information sent with the treatment case information.

2. The method according to claim 1 wherein the identification information stored in the memory of the license media RFID transponder comprises a unique number of the at least one RFID interrogator and a serial number of the at least one scanner.

3. The method according to claim 2 wherein at least a portion of identification information stored in the memory of the license media transponder is encrypted.

4. The method according to claim 1, further comprising providing the at least one RFID interrogator with an auxiliary identification means.

5. The method according to claim 4 wherein the auxiliary identification means comprises an RFID transponder.

6. The method according to claim 5 wherein the second information comprises a unique number of the RFID transponder.

7. The method according to claim 1, further comprising providing the at least on scanner with an auxiliary identification means.

8. The method according to claim 7 wherein the auxiliary identification means comprises a scanner's RFID transponder having a memory.

9. The method according to claim 8, further comprising storing in the memory of the scanner's RFID transponder an identification information referring to the scanner and to its setup.

10. The method according to claim 1 wherein the system is a dental computed radiography system.

11. A system for obtaining an X-ray image of a patient, comprising:

one or more information carrier plates exposed to X-rays to obtain the X-ray image of the patient, each information carrier plate having an affixed RFID transponder provided with a memory for storing temporary and permanent information;

at least one RFID interrogator operable to read and write the temporary information stored in the memory of the RFID transponder;

at least one processing and acquisition station in communication with the at least one RFID interrogator;

at least one scanner in communication with the at least one processing and acquisition station, the at least one scanner provided with a scanner's scanner RFID interrogator having a memory;

a license media provided with a license media RFID transponder having a memory for storing information, the license media adapted for communication with the at least one processing and acquisition station, the at least one RFID interrogator, and the at least one scanner; and wherein the scanner RFID interrogator includes means to compare information stored in the memory of the scanner RFID interrogator with information stored in the memory of the license media RFID transponder, and the scanner scans the one or more information carrier plates if the information stored in the memory of the scanner RFID interrogator matches the information stored in the memory of the license media RFID transponder, wherein the memory of the license media RFID transponder is provided with a plurality of slots allocated for storing at least of a first information associated with an amount of valid licenses permitting use of the at least one RFID interrogator and the at least one scanner, for storing of a second information associated with identification of the at least one RFID interrogator and for storing of a third information associated with identification of the at least one scanner.

12. The system according to claim 11 wherein the license media comprises a carrier to which is affixed the RFID transponder.

13. The system according to claim 11, in which the carrier is a flat substrate made of a plastic material.

14. The system according to claim 11, in which the carrier is configured as a receptacle and the RFID transponder is secured within the receptacle.

15. The system according to claim 11, in which the second information comprises a unique number of the at least one interrogator and the second information comprises a serial number of the at least one scanner.

16. The system according to claim 11, in which the at least one interrogator is provided with an auxiliary identification means, configured as a removable attachable RFID transponder.

17. The system according to claim 16, in which the second information comprises a unique number of the RFID transponder.

18. The system according to claim 11, in which the at least one scanner is provided with an auxiliary identification means, configured as a removable attachable RFID transponder.

19. The system according to claim 18, in which the third information comprises an identification information referring to the at least one scanner and to its setup.

20. The system according to claim 18, in which the RFID transponder is removable attached to a chassis of the at least one scanner.

21. The system according to claim 11, in which at least a portion of the information stored in the license media is encrypted.

22. The system according to claim 11, in which the system is a dental computed radiography system.

* * * * *

UNITED STATES PATENT AND TRADEMARK OFFICE
CERTIFICATE OF CORRECTION

| | |
|---|---|
| PATENT NO. | : 8,833,647 B2 |
| APPLICATION NO. | : 13/563777 |
| DATED | : September 16, 2014 |
| INVENTOR(S) | : Amir Berger et al. |

Page 1 of 1

It is certified that error appears in the above-identified patent and that said Letters Patent is hereby corrected as shown below:

In the Claims,

Column 19, line 56     Please delete the word "scanner's"

Signed and Sealed this
Nineteenth Day of May, 2015

Michelle K. Lee
*Director of the United States Patent and Trademark Office*